United States Patent
Rauhala

(10) Patent No.: US 10,265,022 B2
(45) Date of Patent: Apr. 23, 2019

(54) DETERMINING BIOMETRICS UTILIZING A DISPLAY-EMBEDDED DISTANCE-MEASURING SENSOR

(71) Applicant: Jyri Kalervo Rauhala, Espoo (FI)

(72) Inventor: Jyri Kalervo Rauhala, Espoo (FI)

(73) Assignee: Nokia Technologies Oy, Espoo (FI)

(*) Notice: Subject to any disclaimer, the term of this patent is extended or adjusted under 35 U.S.C. 154(b) by 5 days.

(21) Appl. No.: 13/663,682

(22) Filed: Oct. 30, 2012

(65) Prior Publication Data
US 2014/0121982 A1    May 1, 2014

(51) Int. Cl.
*A61B 5/00* (2006.01)
*A61B 5/11* (2006.01)
*G06F 19/00* (2018.01)
*A61B 5/0205* (2006.01)
*A61B 5/021* (2006.01)

(52) U.S. Cl.
CPC .......... *A61B 5/6898* (2013.01); *A61B 5/1102* (2013.01); *A61B 5/1126* (2013.01); *A61B 5/1128* (2013.01); *G06F 19/3418* (2013.01); *A61B 5/0022* (2013.01); *A61B 5/021* (2013.01); *A61B 5/02055* (2013.01); *A61B 2562/046* (2013.01)

(58) Field of Classification Search
None
See application file for complete search history.

(56) References Cited

U.S. PATENT DOCUMENTS

| | | | |
|---|---|---|---|
| 3,348,050 A | * | 10/1967 | Bez ........................ G01S 3/787 250/203.1 |
| 2008/0262364 A1 | * | 10/2008 | Aarts ............................ 600/509 |
| 2010/0217139 A1 | | 8/2010 | Pinter et al. |
| 2011/0054277 A1 | | 3/2011 | Pinter et al. |
| 2011/0257546 A1 | | 10/2011 | Gozzini et al. |
| 2012/0022385 A1 | | 1/2012 | Shimuta et al. |
| 2012/0143018 A1 | | 6/2012 | Skidmore et al. |
| 2013/0215042 A1 | | 8/2013 | Messerschmidt et al. |

FOREIGN PATENT DOCUMENTS

| KR | 20060045089 A | | 5/2006 |
|---|---|---|---|
| WO | WO 2010093648 A1 | * | 8/2010 |

OTHER PUBLICATIONS

Ruha, "A Micropower Analog-Digital Heart Rate Detector Chip," Analog Integrated Circuits and Signal Processing, vol. 5, p. 147-168, 1994.*

(Continued)

*Primary Examiner* — G Steven Vanni
(74) *Attorney, Agent, or Firm* — Ditthavong & Steiner, P.C.

(57) ABSTRACT

An approach is provided for processing various sensor data and determining various characteristics associated with a user. A data collection module may process and/or facilitate a processing of sensor data for determining one or more distance measurements between at least one body part of a user and a device. The data collection module may determine one or more biometrical characteristics associated with the user based, at least in part, on the one or more distance measurements.

21 Claims, 10 Drawing Sheets

(56) References Cited

OTHER PUBLICATIONS

Mikhelson, "Remote Sensing of Heart Rate and Patterns of Respiration on a Stationary Subject Using 94-GHz Millimeter-Wave Interferometry," IEEE Transactions on Biomedical Engineering, vol. 58, p. 1671-1677, Jun. 2011.*

Wu, "Contactless and continuous monitoring of heart electric activities through clothes on a sleeping bed," IEEE International Conference on Information Technology and Applications in Biomedicine (ITAB), p. 282-285, 2008.*

Darabiha, "Video-rate stereo depth measurement on programmable hardware," Computer Vision and Pattern Recognition, Proceedings of the IEEE Computer Society Conference, vol. 1, p. I-203, 8 pages, 2003.*

Poh, "Non-contact, automated cardiac pulse measurements using video imaging and blind source separation," Optics express, vol. 18(10), p. 10762-10774, 2010.* https://en.wikipedia.org/wiki/Electrocardiography (2018).*
https://en.wikipedia.org/wiki/Capacitance (2018).*
https://en.wikipedia.org/wiki/Voltage (2018).*

M. J. Gregoski, et al., "Development and Validation of a Smartphone Heart Rate Acquisition Application for Health Promotion and Wellness Telehealth Applications," International Journal of Telemedicine and Applications, vol. 2012 (2012), Article ID 696324, 7 pages.

W. Gruener, "3 Apple Products for the Future Without Steve Jobs," tom's GUIDE Tech for Real Life, Oct. 27, 2011, http://www.tomsguide.com/us/apple-tv-ios-valve-steam-video-game-3d, news-12887.html.

J. Karpen, "Amazing Camera Apps," iPhone Life, Mar.-Apr. 2011, http://www.iphonelife.com/issues/2011March-April/AmazingCameraApps.

Rajbex, "Microcontroller Measures Heart Rate through Fingertip," Instructables, Jun. 22, 2011, http://www.instructables.com/id/Microcontroller-measures-heart-rate-through-finger/.

Jung C., et al.; A Remote Compact Sensor for the Real-Time Monitoring of Human Heartbeat and Respiration Rate; IEEE Transactions on Biomedical Circuits and Systems; Jun. 1, 2009; vol. 3, Nr. 3, pp. 181-188.

Mertz, Leslie; Ultrasound? Fetal Monitoring? Spectrometer? There's an App for That! Biomedical Smart Phone Apps Are Taking Healthcare by storm; IEEE Pulse; Mar. 1, 2012; vol. 3, Nr 2, pp. 16-21.

Klug S., et al.; Displaying computerized ECG recordings and vital signs on Windows Phone 7 smartphones; IEEE Computers in Cardiology; Sep. 26, 2010; pp. 1067-1070.

International Search Report and Written Opinion of corresponding International Application No. PCT/FI2013/050973, dated Jan. 29, 2014, 15 pages.

* cited by examiner

DETERMINING BIOMETRICS UTILIZING A DISPLAY-EMBEDDED DISTANCE-MEASURING SENSOR

BACKGROUND

Service providers (e.g., wireless, cellular, etc.) and device manufacturers are continually challenged to deliver value and convenience to consumers by, for example, providing compelling network services. One area of development has been the integration of sensors and filters on various user devices (e.g., mobile phones, tablets, etc.) for user interface and/or measuring and determining a range of information associated with a user and/or the user's environment. For example, the sensors may include touch sensors, health and wellness sensors, accelerometers, gyroscopes, thermometers, cameras, motion detectors, and the like for capturing and processing various sensor data. Further, various filters and algorithms may be employed in the capturing and processing of the sensor data for determining and presenting various information, for example biometrical characteristics, to the user and/or a service provider. As use of the devices and various sensors become more common, service providers and device manufacturers face significant challenges to enabling the user devices and sensors to determine and provide information to the users and service providers.

SOME EXAMPLE EMBODIMENTS

Therefore, there is a need for an approach for processing various sensor data and determining various characteristics associated with a user.

According to one embodiment, a method comprises processing and/or facilitating a processing of sensor data for determining one or more distance measurements between at least one body part of a user and a device. The method also comprises determining one or more biometrical characteristics associated with the user based, at least in part, on the one or more distance measurements.

According to another embodiment, an apparatus comprising at least one processor, and at least one memory including computer program code, the at least one memory and the computer program code configured to, with the at least one processor, cause, at least in part, the apparatus to process and/or facilitate a processing of sensor data for determining one or more distance measurements between at least one body part of a user and a device. The apparatus is also caused to determine one or more biometrical characteristics associated with the user based, at least in part, on the one or more distance measurements.

According to another embodiment, a computer-readable storage medium carrying one or more sequences of one or more instructions which, when executed by one or more processors, cause, at least in part, an apparatus to process and/or facilitate a processing of sensor data for determining one or more distance measurements between at least one body part of a user and a device. The apparatus is also caused to determine one or more biometrical characteristics associated with the user based, at least in part, on the one or more distance measurements.

According to another embodiment, an apparatus comprises means for processing and/or facilitating a processing of sensor data for determining one or more distance measurements between at least one body part of a user and a device. The apparatus also comprises means for determining one or more biometrical characteristics associated with the user based, at least in part, on the one or more distance measurements.

In addition, for various example embodiments of the invention, the following is applicable: a method comprising facilitating a processing of and/or processing (1) data and/or (2) information and/or (3) at least one signal, the (1) data and/or (2) information and/or (3) at least one signal based, at least in part, on (including derived at least in part from) any one or any combination of methods (or processes) disclosed in this application as relevant to any embodiment of the invention.

For various example embodiments of the invention, the following is also applicable: a method comprising facilitating access to at least one interface configured to allow access to at least one service, the at least one service configured to perform any one or any combination of network or service provider methods (or processes) disclosed in this application.

For various example embodiments of the invention, the following is also applicable: a method comprising facilitating creating and/or facilitating modifying (1) at least one device user interface (UI) element and/or (2) at least one device user interface functionality, the (1) at least one device user interface element and/or (2) at least one device user interface functionality based, at least in part, on data and/or information resulting from one or any combination of methods or processes disclosed in this application as relevant to any embodiment of the invention, and/or at least one signal resulting from one or any combination of methods (or processes) disclosed in this application as relevant to any embodiment of the invention.

For various example embodiments of the invention, the following is also applicable: a method comprising creating and/or modifying (1) at least one device user interface element and/or (2) at least one device user interface functionality, the (1) at least one device user interface element and/or (2) at least one device user interface functionality based at least in part on data and/or information resulting from one or any combination of methods (or processes) disclosed in this application as relevant to any embodiment of the invention, and/or at least one signal resulting from one or any combination of methods (or processes) disclosed in this application as relevant to any embodiment of the invention.

In various example embodiments, the methods (or processes) can be accomplished on the service provider side or on the mobile device side or in any shared way between service provider and mobile device with actions being performed on both sides.

For various example embodiments, the following is applicable: An apparatus comprising means for performing the method of any of the originally filed claims.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings.

DESCRIPTION OF SOME EMBODIMENTS

Examples of a method, apparatus, and computer program for processing various sensor data and determining various characteristics associated with a user. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Although various embodiments are discussed with respect to sensors and/or sensor data for health and wellness characteristics, it is contemplated that embodiments of the approach described herein are applicable to any type of sensors and sensor data for determining environmental, physical, material, location, and the like characteristics.

Figure 1:
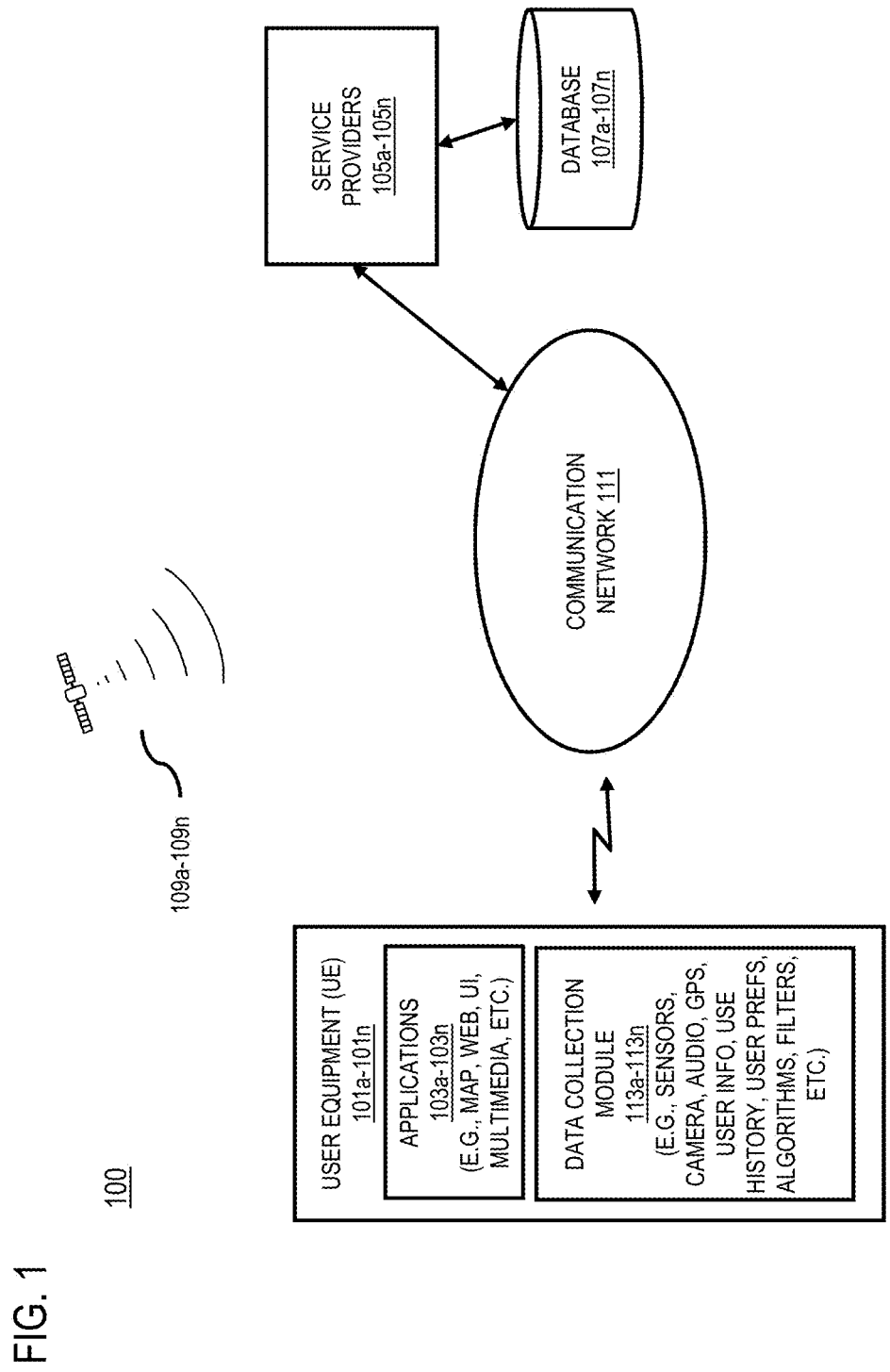
FIG. 1 is a diagram of a system capable of processing various sensor data and determining various characteristics associated with a user, according to an embodiment.

FIG. 1 is a diagram of a system capable of processing various sensor data and determining various characteristics associated with a user, according to an embodiment. As mentioned, users may utilize a range of devices for various purposes; for example, for communication, for entertainment, for productivity, for health and wellness monitoring, etc. where the devices may include various sensors, for example, touch sensors, cameras, accelerometers, gyroscopes, compass, motion detectors, thermometers, and the like. In various situations, the sensors may capture a range of sensor data, which may be utilized to determine valuable information about the user and/or the user's environment. For example, a user may utilize a device (e.g., a mobile phone), which may include various sensors, to determine data associated with his jogging speed, his body temperature, ambient temperature, ambient humidity, galvanic skin response (GSR), heartbeat, and the like. Further, the determined data may be utilized and/or analyzed by various algorithms, applications, and/or service providers to determine and present, for example, health and wellness information to the user. However, the user devices (e.g., tablets, mobile phones, etc.) may or may not include all desirable sensors, for example, due to cost and physical space requirements at the device, thereby limiting availability of certain data to users and/or service providers.

To address, at least these problems, a system 100 of FIG. 1 introduces the capability of processing various sensor data and determining various characteristics associated with a user. In general, users may utilize a range of user devices (e.g., cell phones, smartphones, tablets, etc.) that include various sensors. For example, possible sensors that may be associated with the devices include touch sensors, health and wellness sensors, location sensors (e.g., Global Positioning System (GPS)), light sensors, cameras, proximity sensors, accelerometers, gyroscopes, etc.

Within the context of systems for supporting health and wellness services and/or applications, possible sensors include electrocardiograph (ECG) sensors, photoplethysmograph (PPG) sensors, galvanic skin response (GSR) sensors, electroencephalograph (EEG) sensors, electromyography (EMG) sensors, and the like. However, in addition to these sensors, other available sensors may be utilized to measure certain data and determine information of interest to the user and/or a service provider. For example, electrical characteristics (e.g., capacitance) associated with touch sensors may be utilized to measure a distance (e.g., in z-axis, three dimensional (3D)) between a touch sensor and a body part of a user (e.g., one or more fingertips), wherein the distance measurement may include components indicative of movement and/or jitter relative to the body part, for instance, in x-axis, y-axis, z-axis, relative angles, and the like, wherein the movement and/or jitter may be invisible to naked human eye. In one instance, a user may be prompted to hold a fingertip near and above a device for measuring certain data. For example, variations in distance measurements may be due to variations/fluctuations in the fingertip (e.g., at skin level, in the flesh, etc.), which may be due to blood pressure changes in arteries at the fingertip (e.g., unintentional jitter). In one embodiment, the system 100 may utilize one or more algorithms (e.g., via DSP processes) to filter out movement and/or jitter components that may be deemed to be outside of desired or proper measurement values. For example, a sudden movement may cause a measurement to be well outside of a possible range for a human heartbeat.

In one embodiment, one or more imaging devices may be utilized to capture one or more video recordings and/or a series of images to determine one or more distance variations between a body part and the imaging device (e.g., at an input point). For example, a user may hold a fingertip above a camera lens where a video recording of the fingertip may capture variations; for example, pulsation, jitter, fluctuation, and the like, in the fingertip wherein the variations may be utilized to determine a heartbeat measurement. In another example, a series of images (e.g., picture frames) may be utilized to determine variations in the distance measurement for determining a heartbeat.

In various embodiments, one or more algorithms may be utilized to filter out corrupted/undesired data components, for example, cancelling noise and/or movement/jitter signals deemed outside of a desirable/reasonable range. In one instance, the collected data may include movement of the body part that may be outside of a certain physiological movement characteristic, for example, jitter in the fingertip due to blood pressure corrupted by the fingertip moving a large distance when compared to the jitter.

In one embodiment, the system 100 processes and/or facilitates a processing of sensor data for determining one or more distance measurements between at least one body part of a user and a device. In one embodiment, upon initiation of a sampling period, one or more sensors at a device may be utilized to determine the one or more distance measurements in a z-axis direction (e.g., in a perpendicular direction), wherein the distance is between one or more body parts and the surface of the one or more sensors. In one embodiment, the distance measurements may be with reference to jitter, pulsation, and/or unintentional movements in the body part. In various embodiments, the one or more sensors may be on different devices, which may be utilized for determining the one or more distance measurements, wherein the measurements may be shared among one or more devices, one or more service providers, and the like, for example, via short range wireless communications (e.g., Bluetooth®, Wi-Fi, etc.)

In one embodiment, the system 100 determines one or more biometrical characteristics associated with the user based, at least in part, on the one or more distance measurements. In one embodiment, the one or more distance measurements may include one or more data components for determining one or more biometrical, health, wellness, and the like characteristics associated with the user. In one embodiment, the one or more biometrical characteristics include, at least in part, a heart-rate measurement. For example, the heartbeat may be presented to the user, may be stored at a device, may be shared with one or more applications at the UE 101, may be shared with one or more service providers (e.g., for health and wellness.)

In one embodiment, the system 100 determines the sensor data based, at least in part, on one or more three-dimensional sensors of the device, wherein the one or more distance measurements are based, at least in part, on one or more z-axis values of the sensor data. In one embodiment, the one or more three-dimensional sensors include one or more touch sensors, one or more imaging sensors, one or more motion detection sensors, and the like. In one embodiment, the one or more touch sensors may include one or more touch pads in a touch screen display of the device. For example, the touch sensors may be in one or more layers of a touch sensitive display. In one embodiment, the one or more distance measurements are based, at least in part, on one or more electrical capacitive measurements between the at least one body part and the one or more touch sensors. For example, changes/jitters/movements at a fingertip, due to blood pressure, may result in different capacitance reading, which may be determined as different distance reading, wherein analysis of the frequency of the changes/jitters/movements may indicate a heartbeat (e.g., 65 beats per minute.)

In one embodiment, the system 100 determines one or more parameters for one or more filters for measuring one or more jitters, one or more vibrations, one or more movements, or a combination thereof associated with the at least one body part. In various embodiments, the system 100 may utilize one or more algorithms and/or determine on or more parameters for the one or more algorithms for processing, analyzing, and/or measuring the one or more jitters, vibrations, and/or movements. In one embodiment, the one or more algorithms may filter out one or more undesirable and/or corrupt components of the one or more measurements, for example, noise, voluntary and involuntary movements/jitters outside of an acceptable range, and the like for the measurements. In one embodiment, the sensor data, for example movements that are not substantially in z-axis may be filtered out. For example, if a finger utilized for the measurement is not stationary in x and y dimensions, then the sensor data measurements in the z-axis may be ignored and/or re-taken. In various embodiments, band-pass filtering techniques may be utilized to remove slow finger movements and/or high frequency movements which may be not due to variations of heartbeat (e.g., blood pressure) originated movements. Further, automatic gain control (AGC) may be utilized to measure high peaks and slowly adjust the triggering level for heartbeat pulse detection. Furthermore, leading edges of main heartbeat pulses may be detected for measuring timing information therefrom. In one embodiment, the measured timing may be analysed (e.g., averaged) for optimizing the user experience, for example, convert the time between peaks to more user friendly scale, typically beats/minute and display the results (e.g., present the heartbeat information based on actual user situation without causing restlessness in the user experience.) In one embodiment, the system 100 can determine context information at another sensor or sensors (e.g., an accelerometer, gyroscope, compass, etc.) to determine the one or more parameters and/or to determine information about various components of the data. For example, data from other sensors may indicate that a device in use for the measurements was moving during the capture of the data, or a camera capture may indicate that the user moved the body part in use for the measurements was moving during the measurements, and the like. In one embodiment, the one or more parameters include one or more sampling rates, one or more touch sensor configurations, or a combination thereof. For example, the sampling rate may be determined and varied at 60 Hz, 120 Hz, and the like. In one embodiment, one or more configurations of the one or more touch sensors may be determined and/or changed, for example, to activate, to deactivate, to change sensitivity levels, and the like. In one embodiment, one or more configurations may be determined for one or more other sensors, for example, imaging devices, motion detectors, and the like.

In one embodiment, the system 100 processes and/or facilitates a processing of the sensor data with the one or more filters to determine a filtered portion of the sensor data. In one embodiment, the one or more parameters and/or algorithms may cause a processing of the data for determining a filtered portion where one or more components of the sensor data may be removed, further processed, altered, checked, and the like. For example, data components that are ambiguous, corrupted, outside of certain boundaries, may be removed, marked, double checked, and the like. In various embodiments, user information may be utilized to further define various parameters of a filter or a filter algorithm. For example, a baseline value range (e.g., min-max) for heartbeat measurements may be established by utilizing information about the user's age, gender, height, weight, physical condition, and the like. Further, various measurements of physiological signals; for example, heart-rate measurements over a certain period of time during various activities, may be utilized to augment and/or establish one or more baseline value ranges.

In one embodiment, the system 100 determines the one or more biometrical characteristics based, at least in part, on the one or more distance measurements associated with the filtered portion of the sensor data. In one embodiment, a filtered portion of the sensor data may be presented to one or more applications, algorithms, modules, service providers, and the like for further evaluations and/or determinations of information items (e.g., determine a heartbeat) associated with the user. For example, the filtered portion of the sensor data may one or more different data components whereby one or more information items may be updated.

In addition, the UE 101 can execute applications 103 as a software client for storing, processing, and/or forwarding the sensor data to other components of the system 100. In one embodiment, the applications 103 may include a sensor manager for performing functions related to providing sensor data, algorithms, and parameters as discussed with respect to the various embodiments of the approach described herein.

As shown in FIG. 1, in one embodiment, the system 100 may include user equipment (UE) 101a-101n (also collectively referred to as UE 101 and/or UEs 101), which may be utilized to execute one or more applications 103a-103n (also collectively referred to as applications 103) including social networking, web browser, multimedia applications, user interface (UI), map application, web client, etc. to communicate with other UEs 101, one or more service providers 105a-105n (also collectively referred to as service providers or service provider 105), one or more GPS satellites 109a-109n (also collectively referred to as GPS satellites 109), and/or with other components of the system 100 directly and/or via communication network 111. In one embodiment, the UEs 101 may include data collection modules 113a-113n (also collectively referred to as data collection module 113) for determining and/or collecting data and/or content associated with the UEs 101, one or more sensors, one or more users of the UEs 101, applications 103, one or more content items (e.g., multimedia content), and the like. In addition, the UEs 101 can execute an application 103 that is a software client for storing, processing, and/or forwarding one or more information items to other components of the system 100.

In various embodiments, the data collection module 113 may include and/or utilize various sensors at a UE 101 for collecting, processing, analyzing, determining, etc. data associated with a UE 101, a user, an environment, and the like. For example, collect and analyze location information, ambient temperature, movement speed, and direction of the device, etc. Further, the sensors may utilize sensor data to measure and/or determine physiological information associated with a user, for example, body temperature, GSR, heartbeat, and the like. In one embodiment, sensor data from a certain sensor may be utilized to determine a range information, for example, a touch sensor may be utilized for detecting a user touch (e.g., at a touch-sensitive display) for a UI application as well as process the data to determine pressure applied by the user touch, temperature of the user body part at a contact point on the display, and the like. In one embodiment, the data collection module 113 may utilize one or more touch-sensors to determine a distance between the one or more touch-sensors (e.g., at a display surface level) and a body part (e.g., a fingertip, tip of nose, an earlobe, etc.) of the user. In one embodiment, the data collection module 113 may utilize one or more algorithms and/or filters for determining one or more parameters/components of the sensor data, whereby one or more characteristics associated with the user may be determined/measured. In one instance, the sensor data may indicate one or more directional components; for example, along an x-axis, y-axis, z-axis, of an angle, etc., associated with one or more distance measurements between a sensor and a user's fingertip, wherein the measurements may include voluntary and involuntary movement/jitter components. In one embodiment, one or more algorithms may operate on the one or more distance measurements to determine one or more biometric characteristics associated with a user, for example, a heartbeat.

The UEs 101 may be any type of mobile terminal, fixed terminal, or portable terminal including a mobile handset, station, unit, device, healthcare diagnostic and testing devices, product testing devices, multimedia computer, glasses/goggles/visors including sensors, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, loud speakers, display monitors, radio broadcast receiver, electronic book device, game device, wrist watch, or any combination thereof, including the accessories and peripherals of these devices, or any combination thereof. It is also contemplated that the UEs can support any type of interface to the user (such as "wearable" circuitry, etc.) Further, the UEs 101 may include various sensors for collecting data associated with a user, a user's environment, and/or with a UE 101, for example, the sensors may determine and/or capture audio, video, images, atmospheric conditions, device location, user mood, ambient lighting, device movement speed and direction, and the like.

In one embodiment, the UE 101 includes a location module/sensor that can determine the UE 101 location (e.g., a user's location). The UE 101 location may be determined by a triangulation system such as a GPS, assisted GPS (A-GPS), Cell of Origin, wireless local area network triangulation, or other location extrapolation technologies. Standard GPS and A-GPS systems can use the one or more satellites 109 to pinpoint the location (e.g., longitude, latitude, and altitude) of the UE 101. A Cell of Origin system can be used to determine the cellular tower that a cellular UE 101 is synchronized with. This information provides a coarse location of the UE 101 because the cellular tower can have a unique cellular identifier (cell-ID) that can be geographically mapped. The location module/sensor may also utilize multiple technologies to detect the location of the UE 101. GPS coordinates can provide finer detail as to the location of the UE 101. In another embodiment, the UE 101 may utilize a local area network (e.g., LAN, WLAN) connection to determine the UE 101 location information, for example, from an Internet source (e.g., a service provider).

By way of example, the communication network 111 of system 100 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

In one embodiment, the service providers 105 may include and/or have access to one or more database 107a-107n (also collectively referred to as database 107), which may include various user information, user profiles, user preferences, one or more profiles of one or more user devices (e.g., device configuration, sensors information, etc.), service providers 105 information, other service providers' information, and the like. In one embodiment, the service providers 105 may include one or more service providers offering one or more services, for example, health and wellness, online shopping, location-based services, navigation services, social networking services (e.g., blogging), media upload, media download, media streaming, account management services, or a combination thereof. Further, the service providers 105 may conduct a search for content items, media items, information, coupons, and the like associated with one or more users, POIs, geo-locations, and the like.

By way of example, the UEs 101 and the service providers 105 may communicate with each other and other components of the communication network 111 using well known, new or still developing protocols. In this context, a protocol includes a set of rules defining how the network nodes within the communication network 111 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

In one embodiment, the UEs 101 and the service providers 105 may interact according to a client-server model. It is noted that the client-server model of computer process interaction is widely known and used. According to the client-server model, a client process sends a message including a request to a server process, and the server process responds by providing a service. The server process may also return a message with a response to the client process. Often the client process and server process execute on different computer devices, called hosts, and communicate via a network using one or more protocols for network communications. The term "server" is conventionally used to refer to the process that provides the service, or the host computer on which the process operates. Similarly, the term "client" is conventionally used to refer to the process that makes the request, or the host computer on which the process operates. As used herein, the terms "client" and "server" refer to the processes, rather than the host computers, unless otherwise clear from the context. In addition, the process performed by a server can be broken up to run as multiple processes on multiple hosts (sometimes called tiers) for reasons that include reliability, scalability, and redundancy, among others. It is also noted that the role of a client and a server is not fixed; in some situations a device may act both as a client and a server, which may be done simultaneously and/or the device may alternate between these roles.

Figure 2:
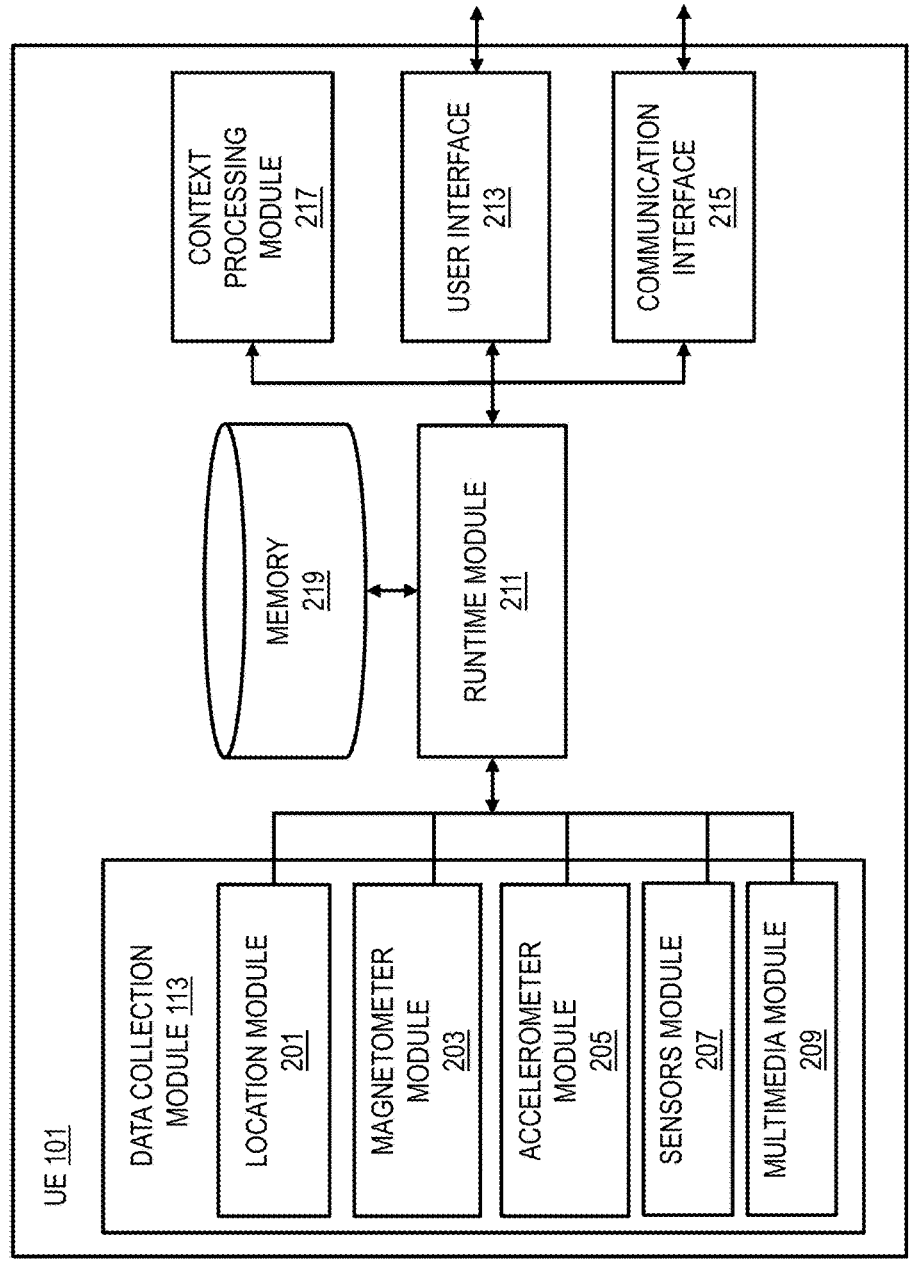
FIG. 2 is a diagram of the components of a user equipment capable of processing various sensor data and determining various characteristics associated with a user, according to an embodiment.

FIG. 2 is a diagram of the components of a user equipment capable of processing various sensor data and determining various characteristics associated with a user, according to an embodiment. By way of example, a UE 101 includes one or more components for utilizing various sensors for collecting, processing, and determining various sensor data. It is contemplated that the functions of these components may be combined in one or more components or performed by other components of equivalent functionality. In this embodiment, the UE 101 includes a data collection module 113 that may include one or more location modules 201, magnetometer modules 203, accelerometer modules 205, sensors modules 207, and multimedia modules 209. Further, the UE 101 may also include a runtime module 211 to coordinate the use of other components of the UE 101, a user interface 213, a communication interface 215, a context processing module 217, and memory 219. The applications 103 of the UE 101 can execute on the runtime module 211 utilizing the components of the UE 101.

The location module 201 can determine a user's location, for example, via location of a UE 101. The user's location can be determined by a triangulation system such as GPS, assisted GPS (A-GPS), Cell of Origin, or other location extrapolation technologies. Standard GPS and A-GPS systems can use satellites 109 to pinpoint the location of a UE 101. A Cell of Origin system can be used to determine the cellular tower that a cellular UE 101 is synchronized with. This information provides a coarse location of the UE 101 because the cellular tower can have a unique cellular identifier (cell-ID) that can be geographically mapped. The location module 201 may also utilize multiple technologies to detect the location of the UE 101. Location coordinates (e.g., GPS coordinates) can give finer detail as to the location of the UE 101 when media is captured. In one embodiment, GPS coordinates are stored as context information in the memory 219 and are available to the context processing module 217, the data collection module 113, the service providers 105, and/or to other entities of the system 100 (e.g., via the communication interface 215.) Moreover, in certain embodiments, the GPS coordinates can include altitude information to provide an elevation height measurement. In other embodiments, the altitude can be determined using another type of altimeter. In certain embodiments, the location module 201 may be utilized for determining location of one or more UEs 101 in an indoor space, for example, by utilizing one or more signals from one or more UEs 101, one or more components of one or more local area networks, one or more indoor positioning systems, or a combination thereof.

The magnetometer module 203 can be used in finding horizontal orientation of the UE 101. A magnetometer is an instrument that can measure the strength and/or direction of a magnetic field. Using the same approach as a compass, the magnetometer is capable of determining the direction of a UE 101 using the magnetic field of the Earth. The front of a media capture device (e.g., a camera) can be marked as a reference point in determining direction. Thus, if the magnetic field points north compared to the reference point, the angle the UE 101 reference point is from the magnetic field is known. Simple calculations can be made to determine the direction of the UE 101. In one embodiment, horizontal directional data obtained from a magnetometer can be stored in memory 219, made available to other modules and/or applications 103 of the UE 101, and/or transmitted via the communication interface 215 to one or more entities of the system 100.

The accelerometer module 205 can be used to determine vertical orientation of the UE 101. An accelerometer is an instrument that can measure acceleration. Using a three-axis accelerometer, with axes x, y, and z, provides the acceleration in three directions with known angles. Once again, the front of a media capture device can be marked as a reference point in determining direction. Because the acceleration due to gravity is known, when a UE 101 is stationary, the accelerometer module 205 can determine the angle the UE 101 is pointed as compared to Earth's gravity. In certain embodiments, the magnetometer module 203 and accelerometer module 205 can be means for ascertaining a perspective of a user. This perspective information may be stored in the memory 219, made available to other modules and/or applications 103 of the UE 101, and/or sent to one or more entities of the system 100.

In various embodiments, the sensors module 207 can process sensor data from various sensors (e.g., touch sensors, GPS, accelerometer, gyroscope, thermometer, microphones, light sensors, etc.) to determine environmental (e.g., atmospheric) conditions surrounding the UE 101, user mood (e.g., hungry, angry, tired, etc.), user physiological measurements (e.g., heartbeat, temperature, GSR, etc.), location information, noise/sounds, lights, and various other information from a range sensors that may be available on one or more devices. For example, the sensors module 207 may detect conditions including humidity, temperature, geo-location, biometrical data of the user, etc. Once again, this information can be stored in the memory 219 and sent to the context processing module 217 and/or to other entities of the system 100. In certain embodiments, information collected from the data collection module 113 can be retrieved by the runtime module 211 and stored in memory 219, made available to other modules and/or applications 103 of the UE 101, and/or sent to one or more entities of the system 100.

In one embodiment, the multimedia module 209 may be utilized to capture various media items, for example, images, video, audio, and the like, wherein the captured media may be submitted to one or more modules and applications of the UE 101, a service provider, and/or a content provider to further processing, storage, sharing, and the like. In one embodiment, a video and/or multiple image frame captures of a user and/or a body part of the user may be utilized for determining various information associated with the user. For example, processing of a video capture of a fingertip of the user may be utilized to measure movements and/or jitter in the fingertip, whereby the jitter information may be utilized to determine one or more physiological information (e.g., heartbeat) of the user.

In one embodiment, the communication interface 215 can be used to communicate with one or more entities of the system 100. Certain communications can be via methods such as an internet protocol, messaging (e.g., SMS, MMS, etc.), or any other communication method (e.g., via the communication network 111). In some examples, a UE 101 can send context information associated with one or more notifications on the UE 101 to the service providers 105, one or more other UEs 101, and/or to other entities of the system 100.

The user interface 213 can include various methods of communication. For example, the user interface 213 can have outputs including a visual component (e.g., a screen), an audio component, a physical component (e.g., vibrations), and other methods of communication. User inputs can include a touch-screen interface, touch sensor pads, a scroll-and-click interface, a button interface, a microphone, etc. Input can be via one or more methods such as voice input, textual input, typed input, touch-screen input, other touch-enabled input, etc.

The context processing module 217 may be utilized in determining context information from the data collection module 113 and/or applications 103 executing on the runtime module 211. This information may be caused to be transmitted, via the communication interface 215, to one or more other UEs 101, to the service providers 105, and/or to other entities of the system 100. In one embodiment, the context processing module 217 may determine various components associated with collected data. For example, the data may include values and/or information associated with different distances and/or angles relative to different axes x, y, z, etc. The context processing module 217 may additionally be utilized as a means for determining information related to the user, an instance of data, device status, a value, a content item, an object, a subject, activities, and the like.

Figure 3:
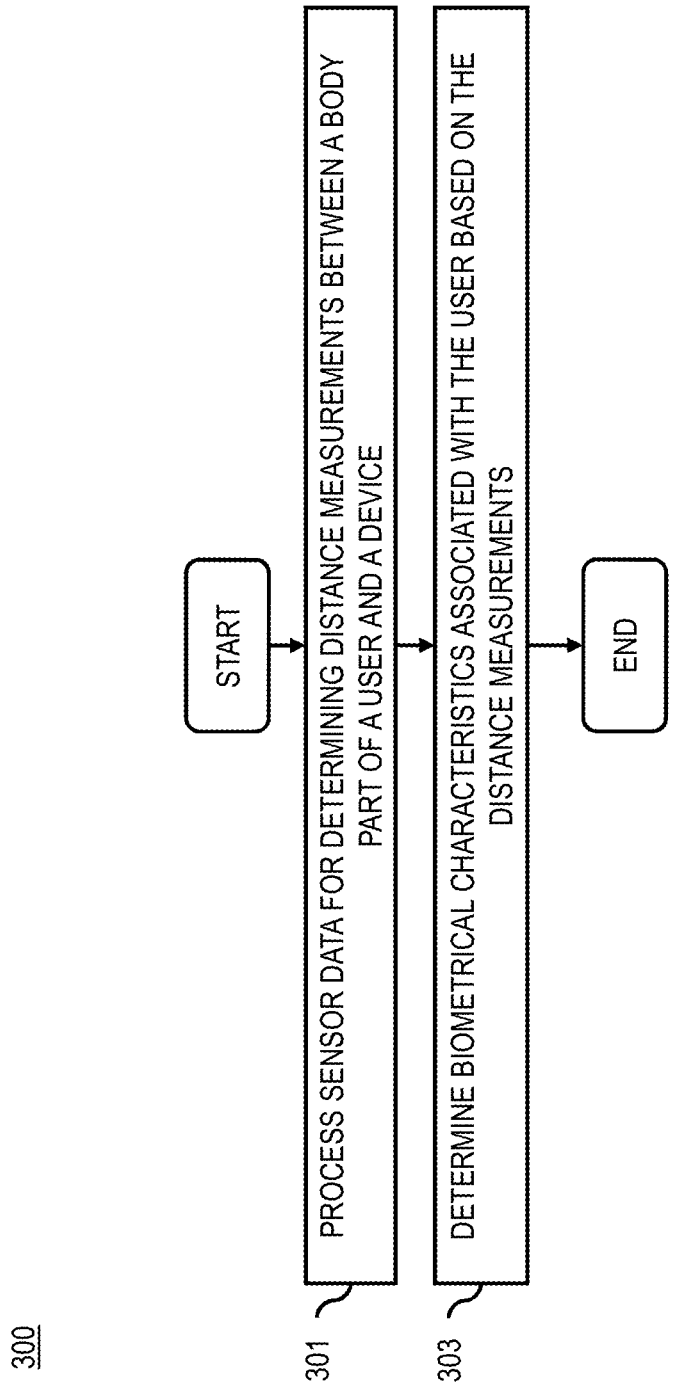
FIG. 3 is a flowchart of a process for, at least, determining distance measurements and biometrical characteristics, according to an embodiment.
Figure 9:
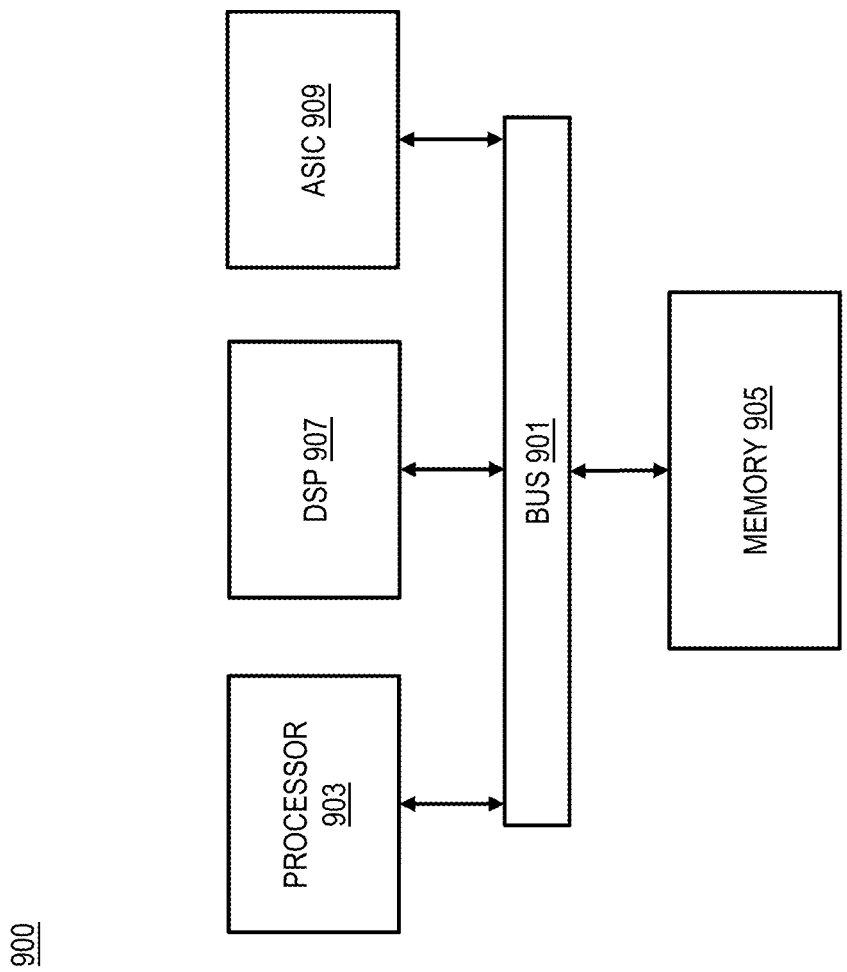
FIG. 9 is a diagram of a chip set that can be used to implement an embodiment of the invention.

FIG. 3 is a flowchart of a process for, at least, determining distance measurements and biometrical characteristics, according to an embodiment. In various embodiments, the data collection module 113 may perform the process 300 and may be implemented in, for instance, a chip set including a processor and a memory as shown in FIG. 9. Further, the data collection module 113, the service providers 105, and/or the UEs 101 can provide means for accomplishing various parts of the process 300 as well as means for accomplishing other processes in conjunction with other components of the system 100. Throughout this process, the data collection module 113 is referred to as completing various portions of the process 300, however, it is understood that other components of the system 100 can perform some of and/or all of the process steps.

In step 301, the data collection module 113 processes and/or facilitates a processing of sensor data for determining one or more distance measurements between at least one body part of a user and a device. In one embodiment, upon initiation of a sampling period, one or more sensors at a device may be utilized to determine the one or more distance measurements in a z-axis direction (e.g., in a perpendicular direction), wherein the distance is between one or more body parts and the surface of the one or more sensors. In one embodiment, the distance measurements may be with reference to jitter, pulsation, and/or unintentional movements in the body part. In various embodiments, the one or more sensors may be on different devices, which may be utilized for determining the one or more distance measurements, wherein the measurements may be shared among one or more devices, one or more service providers, and the like, for example, via short range wireless communications (e.g., Bluetooth®, Wi-Fi, etc.)

In step 303, the data collection module 113 determines one or more biometrical characteristics associated with the user based, at least in part, on the one or more distance measurements. In one embodiment, the one or more distance measurements may include one or more data components for determining one or more biometrical, health, wellness, and the like characteristics associated with the user. In one embodiment, the one or more biometrical characteristics include, at least in part, a heart-rate measurement. For example, the heartbeat may be presented to the user, may be stored at a device, may be shared with one or more applications at the UE 101, may be shared with one or more service providers (e.g., for health and wellness.)

Figure 4:
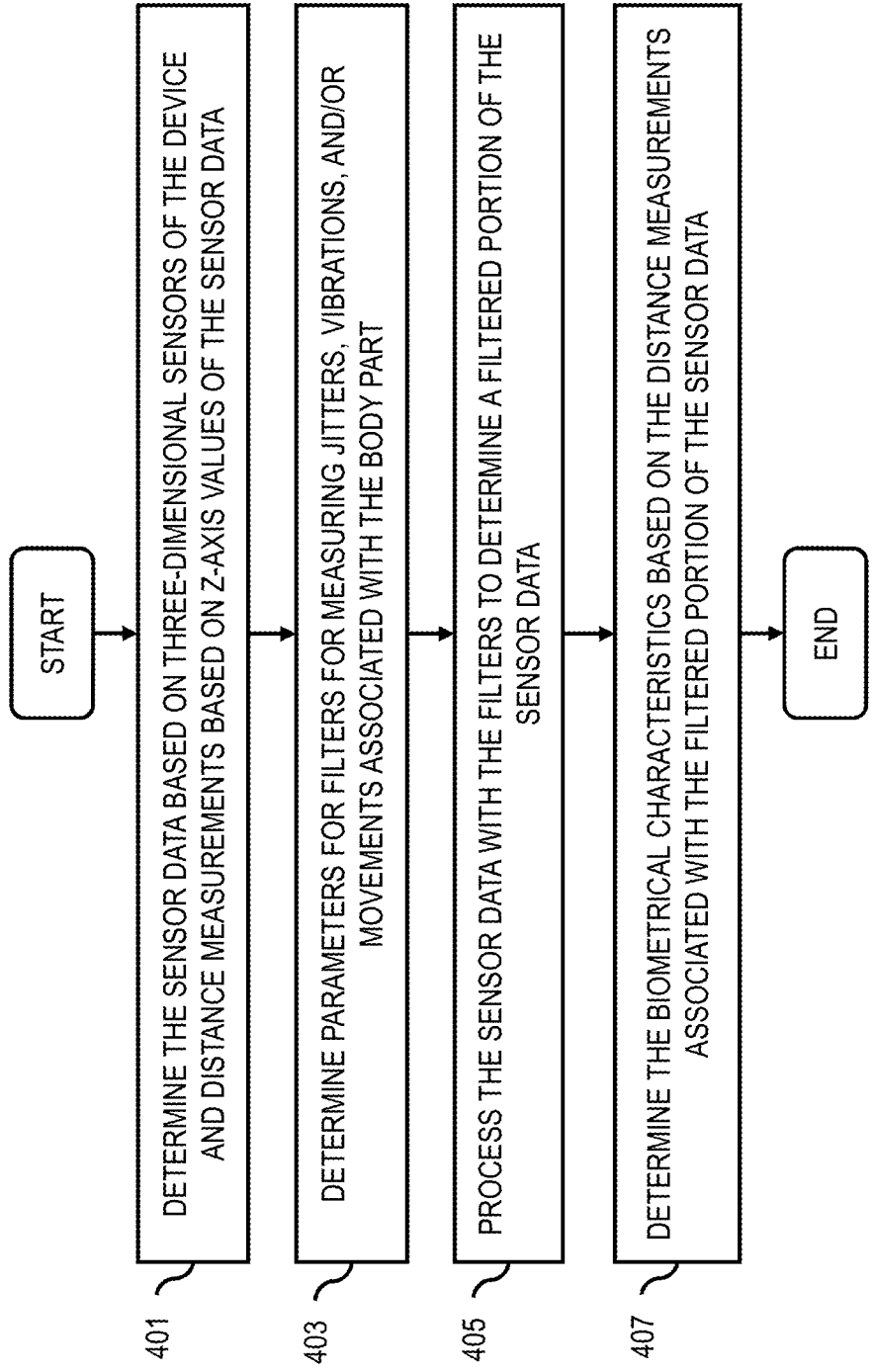
FIG. 4 is a flowchart of a process for, at least, determining sensor data and algorithms, according to various embodiments.

FIG. 4 is a flowchart of a process for, at least, determining sensor data and algorithms, according to various embodiments. In various embodiments, the data collection module 113 may perform the process 400 and may be implemented in, for instance, a chip set including a processor and a memory as shown in FIG. 9. Further, the data collection module 113, the service providers 105, and/or the UEs 101 can provide means for accomplishing various parts of the process 400 as well as means for accomplishing other processes in conjunction with other components of the system 100. Throughout this process, the data collection module 113 is referred to as completing various portions of the process 400, however, it is understood that other components of the system 100 can perform some of and/or all of the process steps.

In step 401, the data collection module 113 determines the sensor data based, at least in part, on one or more three-dimensional sensors of the device, wherein the one or more distance measurements are based, at least in part, on one or more z-axis values of the sensor data. In one embodiment, the one or more three-dimensional sensors include one or more touch sensors, one or more imaging sensors, one or more motion detection sensors, and the like. In one embodiment, the one or more touch sensors may include one or more touch pads in a touch screen display of the device. For example, the touch sensors may be in one or more layers of a touch sensitive display. In one embodiment, the one or more distance measurements are based, at least in part, on one or more electrical capacitive measurements between the at least one body part and the one or more touch sensors. For example, changes/jitters/movements at a fingertip, due to blood pressure, may result in different capacitance reading, which may be determined as different distance reading, wherein analysis of the frequency of the changes/jitters/movements may indicate a heartbeat (e.g., 65 beats per minute.)

In step 403, the data collection module 113 determines one or more parameters for one or more filters for measuring one or more jitters, one or more vibrations, one or more movements, or a combination thereof associated with the at least one body part. In various embodiments, the data collection module 113 may utilize one or more algorithms and/or determine on or more parameters for the one or more algorithms for processing, analyzing, and/or measuring the one or more jitters, vibrations, and/or movements. In one embodiment, the one or more algorithms may filter out one or more undesirable and/or corrupt components of the one or more measurements, for example, noise, voluntary and involuntary movements/jitters outside of an acceptable range, and the like for the measurements. In one embodiment, the sensor data, for example movements that are not substantially in z-axis may be filtered out. For example, if a finger utilized for the measurement is not stationary in x and y dimensions, then the sensor data measurements in the z-axis may be ignored and/or re-taken. In various embodiments, band-pass filtering techniques may be utilized to remove slow finger movements and/or high frequency movements which may be not due to variations of heartbeat (e.g., blood pressure) originated movements. Further, automatic gain control (AGC) may be utilized to measure high peaks and slowly adjust the triggering level for heartbeat pulse detection. Furthermore, leading edges of main heartbeat pulses may be detected for measuring timing information therefrom. In one embodiment, the measured timing may be analysed (e.g., averaged) for optimizing the user experience, for example, convert the time between peaks to more user friendly scale, typically beats/minute and display the results (e.g., present the heartbeat information based on actual user situation without causing restlessness in the user experience.) In one embodiment, the system 100 can determine context information at another sensor or sensors (e.g., an accelerometer, gyroscope, compass, etc.) to determine the one or more parameters and/or to determine information about various components of the data. For example, data from other sensors may indicate that a device in use for the measurements was moving during the capture of the data, or a camera capture may indicate that the user moved the body part in use for the measurements was moving during the measurements, and the like. In one embodiment, the one or more parameters include one or more sampling rates, one or more touch sensor configurations, or a combination thereof. For example, the sampling rate may be determined and varied at 60 Hz, 120 Hz, and the like. In one embodiment, one or more configurations of the one or more touch sensors may be determined and/or changed, for example, to activate, to deactivate, to change sensitivity levels, and the like. In one embodiment, one or more configurations may be determined for one or more other sensors, for example, imaging devices, motion detectors, and the like.

In step 405, the data collection module 113 processes and/or facilitates a processing of the sensor data with the one or more filters to determine a filtered portion of the sensor data. In one embodiment, the one or more parameters and/or algorithms may cause a processing of the data for determining a filtered portion where one or more components of the sensor data may be removed, further processed, altered, checked, and the like. For example, data components that are ambiguous, corrupted, outside of certain boundaries, may be removed, marked, double checked, and the like. In various embodiments, user information may be utilized to further define various parameters of a filter or a filter algorithm. For example, a baseline value range (e.g., min-max) for heartbeat measurements may be established by utilizing information about the user's age, gender, height, weight, physical condition, and the like. Further, various measurements of physiological signals; for example, heart-rate measurements over a certain period of time during various activities, may be utilized to augment and/or establish one or more baseline value ranges.

In step 407, the data collection module 113 determines the one or more biometrical characteristics based, at least in part, on the one or more distance measurements associated with the filtered portion of the sensor data. In one embodiment, a filtered portion of the sensor data may be presented to one or more applications, algorithms, modules, service providers, and the like for further evaluations and/or determinations of information items (e.g., determine a heartbeat) associated with the user. For example, the filtered portion of the sensor data may one or more different data components whereby one or more information items may be updated.

Figure 5:
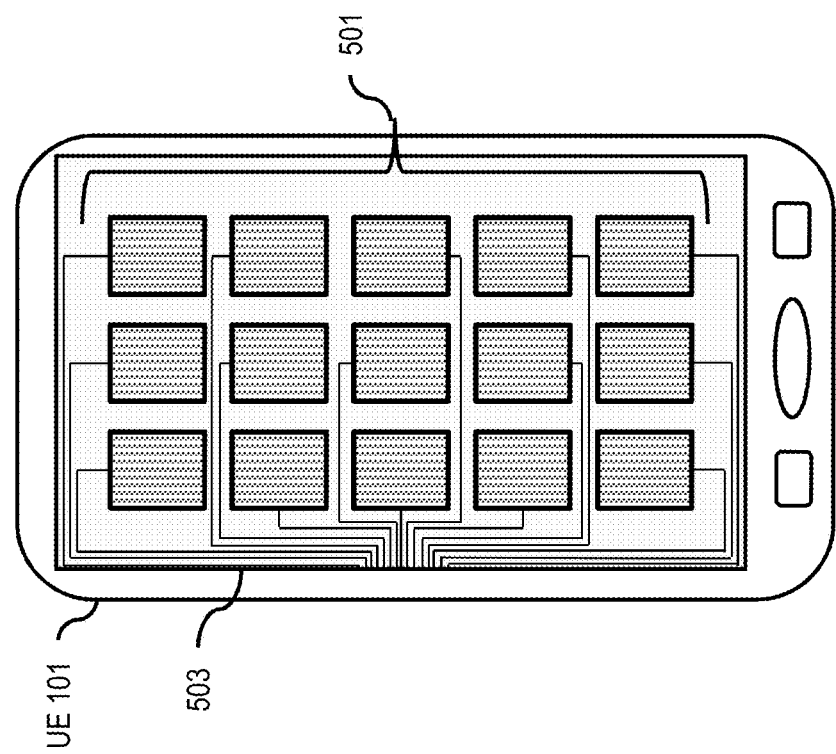
FIG. 5 illustrates multiple touch sensors included at a device, according to an embodiment.

FIG. 5 illustrates multiple touch sensors included at a device, according to an embodiment. In various embodiments, a UE 101 may include a plurality of sensors 501 (e.g., touch sensors), which may be included/implemented in one or more portions of the UE 101. In one embodiment, the sensors 501 may be embedded in a layer component 503 (e.g., of a display device) on the UE 101, wherein the sensors may be utilized by various modules and/or applications for various functionalities at the UE 101. For example, sensors 501 may be utilized as touch sensors for UI applications, wherein one or more sensor data may be collected by one or more modules, one or more applications, one or more other sensors, and the like. Further, the sensor data may be processed and/or analyzed at the UE 101, at one or more other UEs 101, at a service provider, and the like. In various embodiments, the plurality of the sensors 501 may be determined by UE 101 design, UI granularity configuration, applications 103, and the like.

Figure 6:
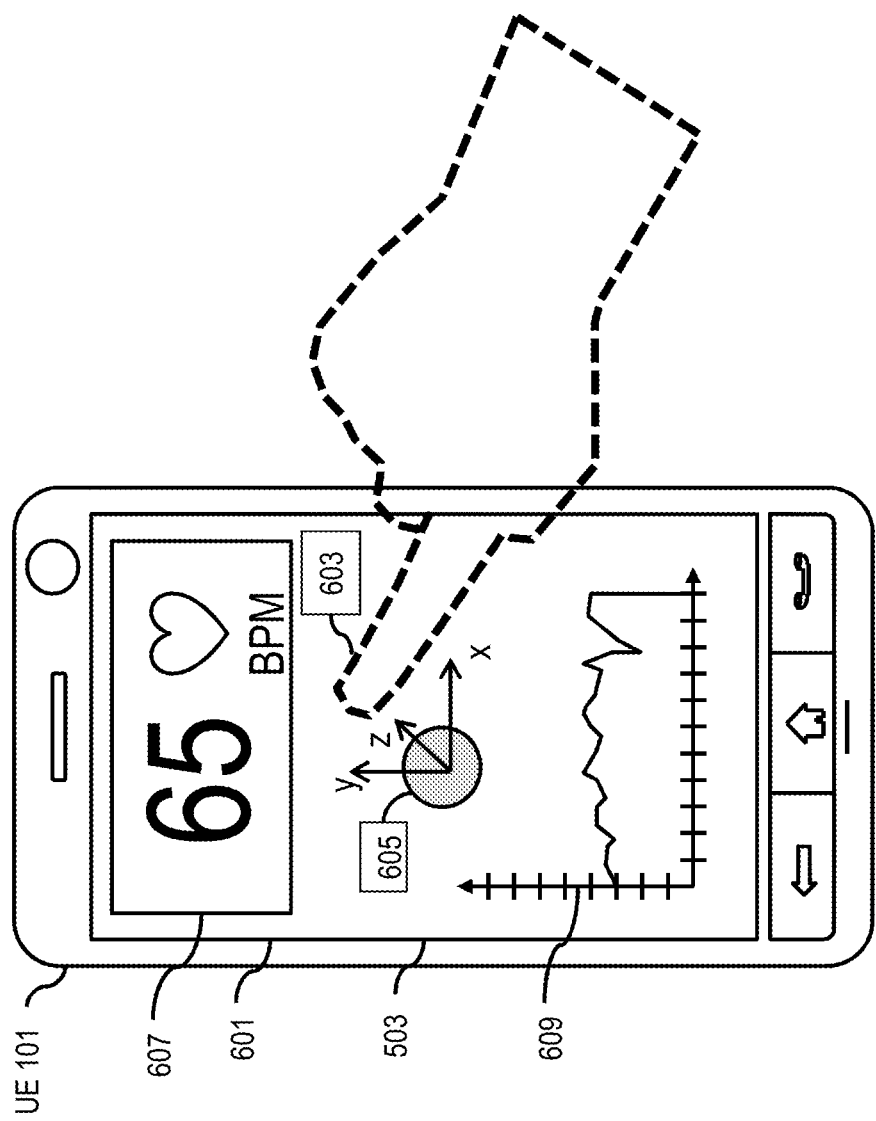
FIGS. 6 and 7 illustrate various UI applications utilized in determining sensor data and biometrical characteristics of a user, according to various embodiments.
Figure 7:
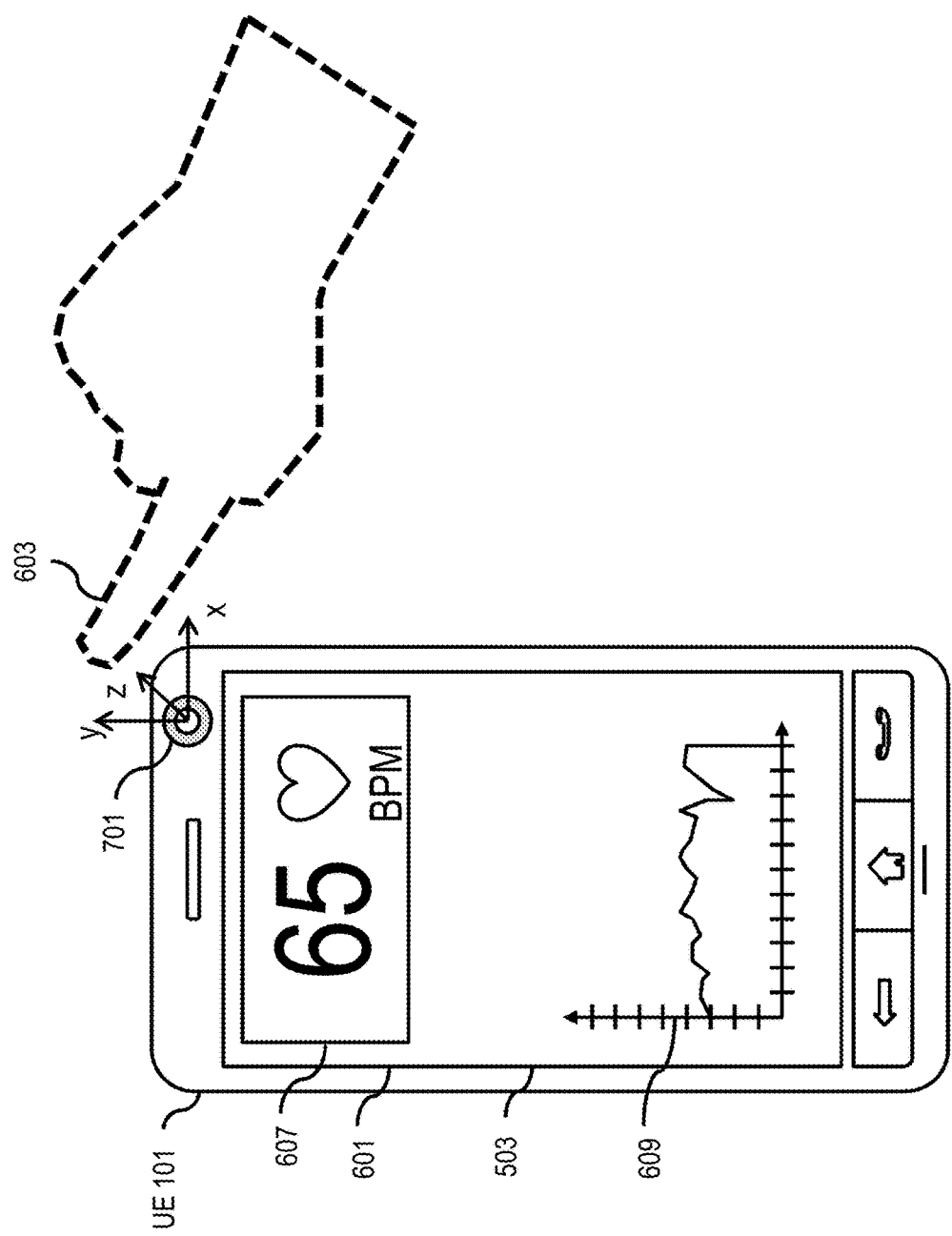

FIGS. 6 and 7 illustrate various UI applications utilized in determining sensor data and biometrical characteristics of a user, according to various embodiments.

FIG. 6 depicts UE 101 including UI 601 wherein a user utilizes a body part 603, for example a finger, to interface with the one or more sensors 501 via a UI target point 605. It is noted that as the one or more sensors 501 may be implemented in multiple locations at the UE 101 (e.g., throughout a display area), the UI target point 605 may be presented to the user as a focal point where the user may be able to maintain a substantially stable position so that the sensors may detect and determine one or more sensor data. In one embodiment, the one or more sensors 501 may detect and determine one or more sensor measurements where the measurements may include one or more distance measurements between the user body part 603 and the one or more sensors 501 at the UE 101, wherein the one or more distance measurements may include data components in the x-axis, y-axis, z-axis directions and/or angle measurements with respect to one or more points (e.g., jittering, fluctuating, pulsating, etc.) on the body part 603 and one or more points at the one or more sensors 501. In one embodiment, the data collection module 113 may utilize a multiple of sensors 501 to measure various data points, which may be aggregated, processed, and/or analyzed for determining one or more data sets. For example, several sensors 501 near the UI target point 605 may be utilized to collect a range of measurements, which may be utilized to render a more accurate and/or complete data set. In one embodiment, the data collection module 113 may utilize one or more other sensors (e.g., a camera) in conjunction with the one or more sensors 501 for determining various sensor data and/or measurements. In one embodiment, the one or more sensors 501 utilize electrical capacitance properties between the body part 603 and the one or more sensors to determine the measurements. In various embodiments, the data collection module 113 may utilize one or more algorithms and/or applications for measuring the one or more distance measurements, at various sampling rates (e.g., 60 Hz, 120 Hz, etc.), and determining one or more biometrical characteristics associated with the user. For example, the biometrical characteristics may include a heartbeat rate, which may be presented via one or more UI components 607 and/or 609.

FIG. 7 depicts the UE 101 including the UI 601 wherein a user utilizes the body part 603, for example a finger, to interface with a sensor 701, wherein the sensor may include one or more imaging sensors. For example, the sensor 701 may be a camera lens whereby a video recording and/or a plurality of images, including 3D spatial information, may be captured and processed for determining a distance between the body part 603 and the sensor 701. In various embodiments, data collection module 113 may utilize one or more algorithms and/or applications to determine a sampling rate (e.g., image frame capture, video recording speed, etc.) for collecting data samples including data components appropriate for determining the one or more distance measurements.

The processes described herein for processing various sensor data and determining various characteristics associated with a user may be advantageously implemented via software, hardware, firmware, or a combination of software and/or firmware and/or hardware. For example, the processes described herein, may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed below.

Figure 8:
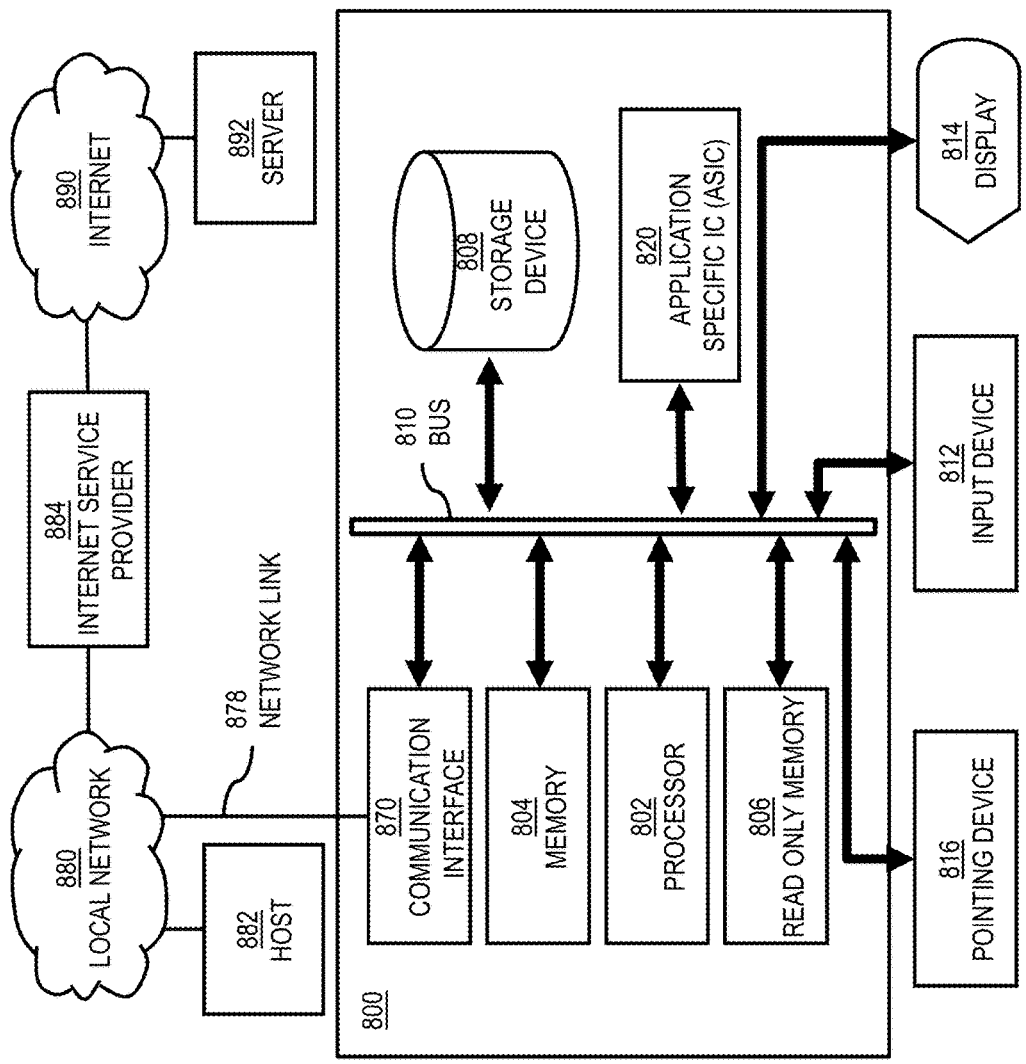
FIG. 8 is a diagram of hardware that can be used to implement an embodiment of the invention.

FIG. 8 illustrates a computer system 800 upon which an embodiment of the invention may be implemented. Although computer system 800 is depicted with respect to a particular device or equipment, it is contemplated that other devices or equipment (e.g., network elements, servers, etc.) within FIG. 8 can deploy the illustrated hardware and components of system 800. Computer system 800 is programmed (e.g., via computer program code or instructions) to process various sensor data and determine various characteristics associated with a user as described herein and includes a communication mechanism such as a bus 810 for passing information between other internal and external components of the computer system 800. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 800, or a portion thereof, constitutes a means for performing one or more steps of processing various sensor data and determining various characteristics associated with a user.

A bus 810 includes one or more parallel conductors of information so that information is transferred quickly among devices coupled to the bus 810. One or more processors 802 for processing information are coupled with the bus 810.

A processor (or multiple processors) 802 performs a set of operations on information as specified by computer program code related to processing various sensor data and determining various characteristics associated with a user. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 810 and placing information on the bus 810. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 802, such as a sequence of operation codes, constitute processor instructions, also called computer system instructions or, simply, computer instructions. Processors may be implemented as mechanical, electrical, magnetic, optical, chemical or quantum components, among others, alone or in combination.

Computer system 800 also includes a memory 804 coupled to bus 810. The memory 804, such as a random access memory (RAM) or any other dynamic storage device, stores information including processor instructions for processing various sensor data and determining various characteristics associated with a user. Dynamic memory allows information stored therein to be changed by the computer system 800. RAM allows a unit of information stored at a location called a memory address to be stored and retrieved independently of information at neighboring addresses. The memory 804 is also used by the processor 802 to store temporary values during execution of processor instructions. The computer system 800 also includes a read only memory (ROM) 806 or any other static storage device coupled to the bus 810 for storing static information, including instructions, that is not changed by the computer system 800. Some memory is composed of volatile storage that loses the information stored thereon when power is lost. Also coupled to bus 810 is a non-volatile (persistent) storage device 808, such as a magnetic disk, optical disk or flash card, for storing information, including instructions, that persists even when the computer system 800 is turned off or otherwise loses power.

Information, including instructions for processing various sensor data and determining various characteristics associated with a user, is provided to the bus 810 for use by the processor from an external input device 812, such as a keyboard containing alphanumeric keys operated by a human user, or a sensor. A sensor detects conditions in its vicinity and transforms those detections into physical expression compatible with the measurable phenomenon used to represent information in computer system 800. Other external devices coupled to bus 810, used primarily for interacting with humans, include a display device 814, such as a cathode ray tube (CRT), a liquid crystal display (LCD), a light emitting diode (LED) display, an organic LED (OLED) display, a plasma screen, or a printer for presenting text or images, and a pointing device 816, such as a mouse, a trackball, cursor direction keys, or a motion sensor, for controlling a position of a small cursor image presented on the display 814 and issuing commands associated with graphical elements presented on the display 814. In some embodiments, for example, in embodiments in which the computer system 800 performs all functions automatically without human input, one or more of external input device 812, display device 814, and pointing device 816 is omitted.

In the illustrated embodiment, special purpose hardware, such as an application specific integrated circuit (ASIC) 820, is coupled to bus 810. The special purpose hardware is configured to perform operations not performed by processor 802 quickly enough for special purposes. Examples of ASICs include graphics accelerator cards for generating images for display 814, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 800 also includes one or more instances of a communications interface 870 coupled to bus 810. Communication interface 870 provides a one-way or two-way communication coupling to a variety of external devices that operate with their own processors, such as printers, scanners, and external disks. In general the coupling is with a network link 878 that is connected to a local network 880 to which a variety of external devices with their own processors are connected. For example, communication interface 870 may be a parallel port or a serial port or a universal serial bus (USB) port on a personal computer. In some embodiments, communications interface 870 is an integrated services digital network (ISDN) card or a digital subscriber line (DSL) card or a telephone modem that provides an information communication connection to a corresponding type of telephone line. In some embodiments, a communication interface 870 is a cable modem that converts signals on bus 810 into signals for a communication connection over a coaxial cable or into optical signals for a communication connection over a fiber optic cable. As another example, communications interface 870 may be a local area network (LAN) card to provide a data communication connection to a compatible LAN, such as Ethernet. Wireless links may also be implemented. For wireless links, the communications interface 870 sends or receives or both sends and receives electrical, acoustic, or electromagnetic signals, including infrared and optical signals that carry information streams, such as digital data. For example, in wireless handheld devices, such as mobile telephones like cell phones, the communications interface 870 includes a radio band electromagnetic transmitter and receiver called a radio transceiver. In certain embodiments, the communications interface 870 enables connection to the communication network 111 for processing various sensor data and determining various characteristics associated with a user.

The term "computer-readable medium" as used herein refers to any medium that participates in providing information to processor 802, including instructions for execution. Such a medium may take many forms, including, but not limited to computer-readable storage medium (e.g., non-volatile media, volatile media), and transmission media. Non-transitory media, such as non-volatile media, include, for example, optical or magnetic disks, such as storage device 808. Volatile media include, for example, dynamic memory 804. Transmission media include, for example, twisted pair cables, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization, or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 820.

Network link 878 typically provides information communication using transmission media through one or more networks to other devices that use or process the information. For example, network link 878 may provide a connection through local network 880 to a host computer 882 or to equipment 884 operated by an Internet Service Provider (ISP). ISP equipment 884 in turn provides data communication services through the public, world-wide packet-switching communication network of networks now commonly referred to as the Internet 890.

A computer called a server host 892 connected to the Internet hosts a process that provides a service in response to information received over the Internet. For example, server host 892 hosts a process that provides information representing video data for presentation at display 814. It is contemplated that the components of system 800 can be deployed in various configurations within other computer systems, e.g., host 882 and server 892.

At least some embodiments of the invention are related to the use of computer system 800 for implementing some or all of the techniques described herein. According to one embodiment of the invention, those techniques are performed by computer system 800 in response to processor 802 executing one or more sequences of one or more processor instructions contained in memory 804. Such instructions, also called computer instructions, software and program code, may be read into memory 804 from another computer-readable medium such as storage device 808 or network link 878. Execution of the sequences of instructions contained in memory 804 causes processor 802 to perform one or more of the method steps described herein. In alternative embodiments, hardware, such as ASIC 820, may be used in place of or in combination with software to implement the invention. Thus, embodiments of the invention are not limited to any specific combination of hardware and software, unless otherwise explicitly stated herein.

The signals transmitted over network link 878 and other networks through communications interface 870, carry information to and from computer system 800. Computer system 800 can send and receive information, including program code, through the networks 880, 890 among others, through network link 878 and communications interface 870. In an example using the Internet 890, a server host 892 transmits program code for a particular application, requested by a message sent from computer 800, through Internet 890, ISP equipment 884, local network 880, and communications interface 870. The received code may be executed by processor 802 as it is received, or may be stored in memory 804 or in storage device 808 or any other non-volatile storage for later execution, or both. In this manner, computer system 800 may obtain application program code in the form of signals on a carrier wave.

Various forms of computer readable media may be involved in carrying one or more sequence of instructions or data or both to processor 802 for execution. For example, instructions and data may initially be carried on a magnetic disk of a remote computer such as host 882. The remote computer loads the instructions and data into its dynamic memory and sends the instructions and data over a telephone line using a modem. A modem local to the computer system 800 receives the instructions and data on a telephone line and uses an infra-red transmitter to convert the instructions and data to a signal on an infra-red carrier wave serving as the network link 878. An infrared detector serving as communications interface 870 receives the instructions and data carried in the infrared signal and places information representing the instructions and data onto bus 810. Bus 810 carries the information to memory 804 from which processor 802 retrieves and executes the instructions using some of the data sent with the instructions. The instructions and data received in memory 804 may optionally be stored on storage device 808, either before or after execution by the processor 802.

FIG. 9 illustrates a chip set or chip 900 upon which an embodiment of the invention may be implemented. Chip set 900 is programmed processing various sensor data and determining various characteristics associated with a user as described herein and includes, for instance, the processor and memory components described with respect to FIG. 8 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set 900 can be implemented in a single chip. It is further contemplated that in certain embodiments the chip set or chip 900 can be implemented as a single "system on a chip." It is further contemplated that in certain embodiments a separate ASIC would not be used, for example, and that all relevant functions as disclosed herein would be performed by a processor or processors. Chip set or chip 900, or a portion thereof, constitutes a means for performing one or more steps of providing user interface navigation information associated with the availability of functions. Chip set or chip 900, or a portion thereof, constitutes a means for performing one or more steps of processing various sensor data and determining various characteristics associated with a user.

In one embodiment, the chip set or chip 900 includes a communication mechanism such as a bus 901 for passing information among the components of the chip set 900. A processor 903 has connectivity to the bus 901 to execute instructions and process information stored in, for example, a memory 905. The processor 903 may include one or more processing cores with each core configured to perform independently. A multi-core processor enables multiprocessing within a single physical package. Examples of a multi-core processor include two, four, eight, or greater numbers of processing cores. Alternatively or in addition, the processor 903 may include one or more microprocessors configured in tandem via the bus 901 to enable independent execution of instructions, pipelining, and multithreading. The processor 903 may also be accompanied with one or more specialized components to perform certain processing functions and tasks such as one or more digital signal processors (DSP) 907, or one or more application-specific integrated circuits (ASIC) 909. A DSP 907 typically is configured to process real-world signals (e.g., sound) in real time independently of the processor 903. Similarly, an ASIC 909 can be configured to performed specialized functions not easily performed by a more general purpose processor. Other specialized components to aid in performing the inventive functions described herein may include one or more field programmable gate arrays (FPGA), one or more controllers, or one or more other special-purpose computer chips.

In one embodiment, the chip set or chip 900 includes merely one or more processors and some software and/or firmware supporting and/or relating to and/or for the one or more processors.

The processor 903 and accompanying components have connectivity to the memory 905 via the bus 901. The memory 905 includes both dynamic memory (e.g., RAM, magnetic disk, writable optical disk, etc.) and static memory (e.g., ROM, CD-ROM, etc.) for storing executable instructions that when executed perform the inventive steps described herein to process various sensor data and determine various characteristics associated with a user. The memory 905 also stores the data associated with or generated by the execution of the inventive steps.

Figure 10:
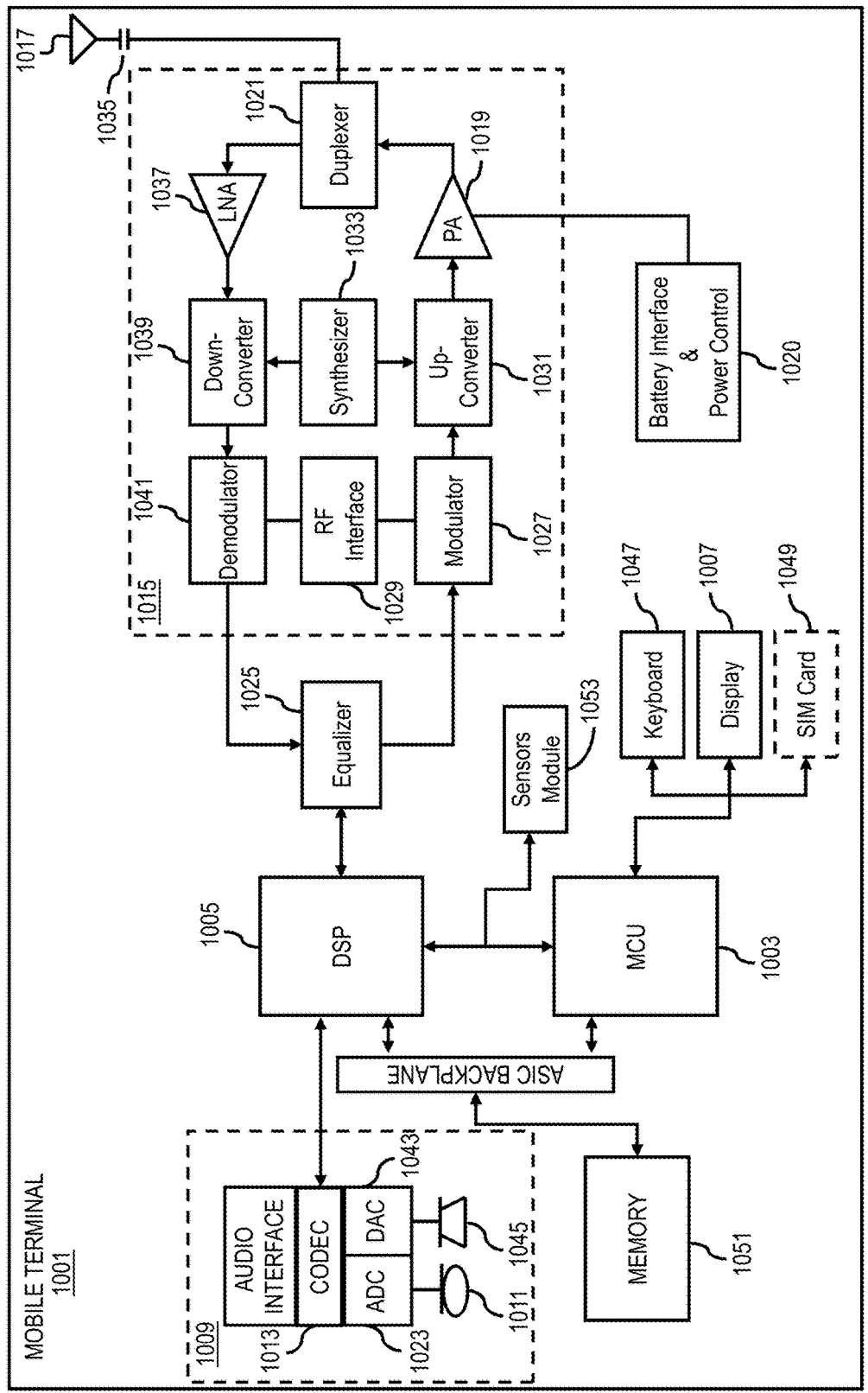
FIG. 10 is a diagram of a mobile terminal (e.g., handset) that can be used to implement an embodiment of the invention.

FIG. 10 is a diagram of exemplary components of a mobile terminal (e.g., handset) for communications, which is capable of operating in the system of FIG. 1, according to one embodiment. In some embodiments, mobile terminal 1001, or a portion thereof, constitutes a means for performing one or more steps of processing various sensor data and determining various characteristics associated with a user. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 1003, a Digital Signal Processor (DSP) 1005, and a receiver/transmitter unit including a microphone gain control unit and a speaker gain control unit. A main display unit 1007 provides a display to the user in support of various applications and mobile terminal functions that perform or support the steps of processing various sensor data and determining various characteristics associated with a user. The display 1007 includes display circuitry configured to display at least a portion of a user interface of the mobile terminal (e.g., mobile telephone). Additionally, the display 1007 and display circuitry are configured to facilitate user control of at least some functions of the mobile terminal. An audio function circuitry 1009 includes a microphone 1011 and microphone amplifier that amplifies the speech signal output from the microphone 1011. The amplified speech signal output from the microphone 1011 is fed to a coder/decoder (CODEC) 1013.

A radio section 1015 amplifies power and converts frequency in order to communicate with a base station, which is included in a mobile communication system, via antenna 1017. The power amplifier (PA) 1019 and the transmitter/modulation circuitry are operationally responsive to the MCU 1003, with an output from the PA 1019 coupled to the duplexer 1021 or circulator or antenna switch, as known in the art. The PA 1019 also couples to a battery interface and power control unit 1020.

In use, a user of mobile terminal 1001 speaks into the microphone 1011 and his or her voice along with any detected background noise is converted into an analog voltage. The analog voltage is then converted into a digital signal through the Analog to Digital Converter (ADC) 1023. The control unit 1003 routes the digital signal into the DSP 1005 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 1025 for compensation of any frequency-dependent impairments that occur during transmission though the air such as phase and amplitude distortion. After equalizing the bit stream, the modulator 1027 combines the signal with a RF signal generated in the RF interface 1029. The modulator 1027 generates a sine wave by way of frequency or phase modulation. In order to prepare the signal for transmission, an up-converter 1031 combines the sine wave output from the modulator 1027 with another sine wave generated by a synthesizer 1033 to achieve the desired frequency of transmission. The signal is then sent through a PA 1019 to increase the signal to an appropriate power level. In practical systems, the PA 1019 acts as a variable gain amplifier whose gain is controlled by the DSP 1005 from information received from a network base station. The signal is then filtered within the duplexer 1021 and optionally sent to an antenna coupler 1035 to match impedances to provide maximum power transfer. Finally, the signal is transmitted via antenna 1017 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 1001 are received via antenna 1017 and immediately amplified by a low noise amplifier (LNA) 1037. A down-converter 1039 lowers the carrier frequency while the demodulator 1041 strips away the RF leaving only a digital bit stream. The signal then goes through the equalizer 1025 and is processed by the DSP 1005. A Digital to Analog Converter (DAC) 1043 converts the signal and the resulting output is transmitted to the user through the speaker 1045, all under control of a Main Control Unit (MCU) 1003 which can be implemented as a Central Processing Unit (CPU).

The MCU 1003 receives various signals including input signals from the keyboard 1047. The keyboard 1047 and/or the MCU 1003 in combination with other user input components (e.g., the microphone 1011) comprise a user interface circuitry for managing user input. The MCU 1003 runs a user interface software to facilitate user control of at least some functions of the mobile terminal 1001 for processing various sensor data and determining various characteristics associated with a user. The MCU 1003 also delivers a display command and a switch command to the display 1007 and to the speech output switching controller, respectively. Further, the MCU 1003 exchanges information with the DSP 1005 and can access an optionally incorporated SIM card 1049 and a memory 1051. In addition, the MCU 1003 executes various control functions required of the terminal. The DSP 1005 may, depending upon the implementation, perform any of a variety of conventional digital processing functions on the voice signals. Additionally, DSP 1005 determines the background noise level of the local environment from the signals detected by microphone 1011 and sets the gain of microphone 1011 to a level selected to compensate for the natural tendency of the user of the mobile terminal 1001.

The CODEC 1013 includes the ADC 1023 and DAC 1043. The memory 1051 stores various data including call incoming tone data and is capable of storing other data including music data received via, e.g., the global Internet. The software module could reside in RAM memory, flash memory, registers, or any other form of writable storage medium known in the art. The memory device 1051 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 1049 carries, for instance, important information, such as the cellular phone number, the carrier supplying service, subscription details, and security information. The SIM card 1049 serves primarily to identify the mobile terminal 1001 on a radio network. The card 1049 also contains a memory for storing a personal telephone number registry, text messages, and user specific mobile terminal settings.

Additionally, sensors module 1053 may include various sensors, for instance, a location sensor, a speed sensor, an audio sensor, an image sensor, a brightness sensor, a biometrics sensor, various physiological sensors, a directional sensor, and the like, for capturing various data associated with the mobile terminal 1001 (e.g., a mobile phone), a user of the mobile terminal 1001, an environment of the mobile terminal 1001 and/or the user, or a combination thereof, wherein the data may be collected, processed, stored, and/or shared with one or more components and/or modules of the mobile terminal 1001 and/or with one or more entities external to the mobile terminal 1001.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A method for determining biometrics, the method comprising:
   receiving, via one or more proximity sensors, one or more touch sensors, or a combination thereof embedded in a display of a device, sensor data gathered over a period of time from distance changes between the display and a body part of a subject, wherein at least some portion of the received sensor data is associated with a biometrical characteristic of another body part of the subject that is not in contact with the device;
   determining, based on the sensor data by at least one processor, moving distances between the body part and the display, wherein the moving distances are along an axis substantially perpendicular to the display and resulted from one or more sensed phenomena correlative with movements of the body part and the biometrical characteristic of the another body part; and
   determining a measurement of the biometrical characteristic of the another body part based, at least in part, on a number of the moving distances within a magnitude range.

2. The method of claim 1, wherein the biometrical characteristics include a heart-rate of the subject, and wherein the body part includes a finger of the subject.

3. The method of claim 2, further comprising:
   determining a frequency of the heart-rate based on the measurement.

4. The method of claim 1, wherein the device is configured to record electrical capacitance measurements or video images.

5. The method of claim 1, wherein at least one of the touch sensors collects data associated with measuring an electrical characteristic utilized in determining a moving distance between the body part and the at least one touch sensor.

6. The method of claim 1, wherein at least one other sensor of the device records images of the body part utilized in determining a moving distance between the body part and the at least one sensor.

7. The method of claim 1, further comprising:
   receiving, utilizing at least one interface of the device, other sensor data gathered over the period of time utilizing the touch sensors, wherein the other sensor data is associated with one or more characteristics other than the biometrical characteristic associated with the subject.

8. The method of claim 1, wherein the body part is a finger, and wherein at least one of the touch sensors collects data associated with measuring an electrical characteristic utilized in determining a moving distance between the body part and the at least one touch sensor.

9. The method of claim 2, further comprising:
   determining one or more moving distances associated with the body part as not stationary in at least one of the x and/or y dimensions in parallel with the display; and
   filtering the one or more moving distances from being counted in the number of the moving distances within the magnitude range.

10. The method of claim 2, wherein determining the biometrical characteristic of the subject includes incorporating, into the algorithm, demographic information and/or other physiological information associated with the subject.

11. An apparatus for determining biometrics, the apparatus comprising:
    at least one processor; and
    at least one memory including computer program code, the at least one memory and the computer program code configured to, with the at least one processor, cause the apparatus to perform at least the following:
    receive, via one or more proximity sensors, one or more touch sensors, or a combination thereof embedded in a display of a device, sensor data gathered over a period of time from distance changes between the display and a body part of a subject, wherein at least some portion of the received sensor data is associated with a biometrical characteristic of another body part of the subject that is not in contact with the device;

determine, based on the sensor data, moving distances, between the body part and the display, wherein the moving distances are along an axis substantially perpendicular to the display and resulted from one or more sensed phenomena correlative with movements of the body part and the biometrical characteristic of the another body part; and determine a measurement of the biometrical characteristic of the another body part based, at least in part, on a number of the moving distances within a magnitude range.

12. The apparatus of claim 11, wherein the biometrical characteristics include a heart-rate of the subject, and wherein the body part includes a finger of the subject.

13. The apparatus of claim 12, wherein the apparatus is further caused to:
determine a frequency of the heart-rate based on the measurement.

14. The apparatus of claim 11, wherein the body part is a finger, and wherein at least one of the touch sensors collects data associated with measuring an electrical characteristic utilized in determining a moving distance between the body part and the at least one touch sensor.

15. The apparatus of claim 11, wherein at least one other sensor of the device records images of the body part utilized in determining a moving distance between the body part and the at least one sensor.

16. The apparatus of claim 12, wherein the apparatus is further caused to:
determining one or more moving distances associated with the body part as not stationary in at least one of the x and/or y dimensions in parallel with the display; and
filtering the one or more moving distances from being counted in the number of the moving distances within the magnitude range.

17. The apparatus of claim 11, wherein the apparatus is further caused to:
receive, utilizing at least one interface of the device, other sensor data gathered over the period of time utilizing the touch sensors, wherein the other sensor data is associated with one or more characteristics other than the biometrical characteristic associated with the subject.

18. A non-transitory computer-readable medium for determining biometrics, the medium carrying one or more sequences of one or more instructions which, when executed by one or more processors, cause an apparatus to at least perform:

receiving proximity sensor data, touch sensor data, or a combination thereof from a device gathered over a period of time from distance changes between the display and a body part of a subject, wherein at least some portion of the received sensor data is associated with a biometrical characteristic of another body part of the subject that is not in contact with the device;

determining, based on the sensor data, moving distances between the body part and the display, wherein the moving distances are along an axis substantially perpendicular to the display and resulted from one or more sensed phenomena correlative with movements of the body part and the biometrical characteristic of the another body part; and determining a measurement of the biometrical characteristic of the another body part based, at least in part, on a number of the moving distances within a magnitude range.

19. The computer readable medium of claim 18, wherein the biometrical characteristics include a heart-rate of the subject, and
wherein the body part includes a finger of the subject.

20. The computer readable medium of claim 19, wherein the apparatus is further caused to at least perform:
determining a frequency of the heart-rate based on the measurement.

21. The computer readable medium method of claim 18, wherein the device is configured to record electrical capacitance measurements or video images.

* * * * *